(12) United States Patent
Davies et al.

(10) Patent No.: US 6,602,882 B1
(45) Date of Patent: Aug. 5, 2003

(54) QUINOLINE DERIVATIVES AND THEIR USE AS ANTIBACTERIAL AGENTS

(75) Inventors: David Thomas Davies, Harlow (GB); Roger Edward Markwell, Harlow (GB); Neil David Pearson, Harlow (GB); Andrew Kenneth Takle, Harlow (GB)

(73) Assignee: SmithKline Beecham p.l.c., Brentford (GB)

( * ) Notice: Subject to any disclaimer, the term of this patent is extended or adjusted under 35 U.S.C. 154(b) by 0 days.

(21) Appl. No.: 09/807,341

(22) PCT Filed: Oct. 11, 1999

(86) PCT No.: PCT/EP99/07766

§ 371 (c)(1),
(2), (4) Date: May 24, 2001

(87) PCT Pub. No.: WO00/21952

PCT Pub. Date: Apr. 20, 2000

(30) Foreign Application Priority Data

Oct. 14, 1998 (GB) .............................. 9822440

(51) Int. Cl.⁷ ................ A61K 31/4375; A61K 31/4709; C07D 401/12; C07D 455/02; C07D 471/04; A61P 31/04

(52) U.S. Cl. ................ 514/300; 514/306; 514/313; 514/248; 514/258; 546/122; 546/138; 546/159; 546/163; 544/235; 544/293

(58) Field of Search ................ 546/163, 159, 546/122, 138; 514/300, 306, 313, 248, 258; 544/235, 293

(56) References Cited

U.S. PATENT DOCUMENTS 4,472,404 A 9/1984 Paxton et al.
5,849,757 A * 12/1998 Takemura .................. 514/312

FOREIGN PATENT DOCUMENTS

| EP | 0 387 510 A | 9/1990 |
|---|---|---|
| EP | 0 497 303 A | 8/1992 |
| EP | 0 875 501 | 4/1998 |
| JP | 04095071 | 3/1992 |
| WO | WO 94/14801 A1 | 7/1994 |
| WO | WO 97/14681 A1 | 4/1997 |
| WO | WO 99 37635 | 7/1999 |
| WO | WO 01/25227 | 4/2001 |

OTHER PUBLICATIONS

Database WPI Week 9219 Derwent Publications Ltd., London, GB: AN 1992–156268 XP002130005 & JP 04 095071 A (Kyorin Pharmaceutical Co. Ltd.), Mar. 27, 1992 abstract.
Chemical Abstracts, vol. 71, No. 21, Nov. 24, 1969 Columbus, Ohio, HS: abstract No. 101730j, Hamana, M. et al.: "Quinolinecarbamates, bactericides and fungicides." p. 337; column 1; XP002130004 abstract & JP 69 018299 A (Kowa Co. Ltd.).

* cited by examiner

Primary Examiner—Evelyn Mei Huang
(74) Attorney, Agent, or Firm—Laura K. Madden; Mary E. McCarthy; Charles M. Kinzig

(57) ABSTRACT

Piperidine derivatives and pharmaceutical derivatives thereof useful in methods of treatment of bacterial infections in mammals, particularly in man.

16 Claims, No Drawings

QUINOLINE DERIVATIVES AND THEIR USE AS ANTIBACTERIAL AGENTS

This application is a 371 of PCT/EP99/07766, filed on Oct. 11, 1999.

This invention relates to novel medicaments, being novel antibacterial compounds and compositions.

JP04095071 discloses piperidyl carbamic acid derivatives for treating dementia by ameliorating memory disturbance.

This invention provides a compound of formula (I) or a pharmaceutically acceptable derivative thereof:

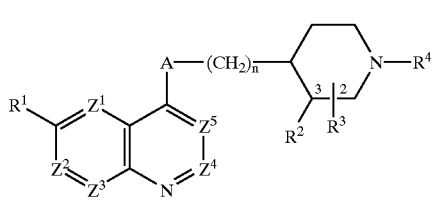

wherein:
one of $Z^1$, $Z^2$, $Z^3$, $Z^4$ and $Z^5$ is N or $CR^{1a}$ and the remainder are CH;

$R^1$ is selected from hydroxy; $(C_{1-6})$alkoxy optionally substituted by $(C_{1-6})$alkoxy, amino, piperidyl, guanidino or amidino optionally N-substituted by one or two $(C_{1-6})$alkyl, acyl or $(C_{1-6})$alkylsulphonyl groups, $NH_2CO$, hydroxy, thiol, $(C_{1-6})$alkylthio, heterocyclylthio, heterocyclyloxy, arylthio, aryloxy, acylthio, acyloxy or $(C_{1-6})$alkylsulphonyloxy; $(C_{1-6})$alkoxy-substituted $(C_{1-6})$alkyl; halogen; $(C_{1-6})$alkyl; $(C_{1-6})$alkylthio; nitro; trifluoromethyl; azido; acyl; acyloxy; acylthio; $(C_{1-6})$alkylsulphonyl; $(C_{1-6})$alkylsulphoxide; arylsulphonyl; arylsulphoxide or an amino, piperidyl, guanidino or amidino group optionally N-substituted by one or two $(C_{1-6})$alkyl, acyl or $(C_{1-6})$alkylsulphonyl groups, or when one of $Z^1$, $Z^2$, $Z^3$, $Z^4$ and $Z^5$ is N, $R^1$ may instead be hydrogen;

$R^{1a}$ is selected from hydrogen and the groups listed above for $R^1$;

either $R^2$ is hydrogen; and $R^3$ is in the 2- or 3-position and is hydrogen or $(C_{1-6})$alkyl or $(C_{2-6})$alkenyl optionally substituted with 1 to 3 groups selected from:
thiol; halogen; $(C_{1-6})$alkylthio; trifluoromethyl; azido; $(C_{1-6})$alkoxycarbonyl; $(C_{1-6})$alkylcarbonyl; $(C_{2-6})$alkenyloxycarbonyl; $(C_{2-6})$alkenylcarbonyl; hydroxy optionally substituted by $(C_{1-6})$alkyl, $(C_{2-6})$alkenyl, $(C_{1-6})$alkoxycarbonyl, $(C_{1-6})$alkylcarbonyl, $(C_{2-6})$alkenyloxycarbonyl, $(C_{2-6})$alkenylcarbonyl or aminocarbonyl wherein the amino group is optionally substituted by $(C_{1-6})$alkyl, $(C_{2-6})$alkenyl, $(C_{1-6})$alkylcarbonyl or $(C_{2-6})$alkenylcarbonyl; amino optionally mono- or disubstituted by $(C_{1-6})$alkoxycarbonyl, $(C_{1-6})$alkylcarbonyl, $(C_{2-6})$alkenyloxycarbonyl, $(C_{2-6})$alkenylcarbonyl, $(C_{1-6})$alkyl, $(C_{2-6})$alkenyl, $(C_{1-6})$alkylsulphonyl, $(C_{2-6})$alkenylsulphonyl or aminocarbonyl wherein the amino group is optionally substituted by $(C_{1-6})$alkyl or $(C_{2-6})$alkenyl; aminocarbonyl wherein the amino group is optionally mono- or disubstituted by $(C_{1-6})$alkyl, $(C_{2-6})$alkenyl, $(C_{1-6})$alkoxycarbonyl, $(C_{1-6})$alkylcarbonyl, $(C_{2-6})$alkenyloxycarbonyl or $(C_{2-6})$alkenylcarbonyl; oxo; $(C_{1-6})$alkylsulphonyl; $(C_{2-6})$alkenylsulphonyl; or $(C_{1-6})$aminosulphonyl wherein the amino group is optionally substituted by $(C_{1-6})$alkyl or $(C_{2-6})$alkenyl;

or when $R^3$ is in the 2-position it may with $R^4$ form a $C_{3-5}$ alkylene group optionally substituted by a group $R^5$ selected from:

$(C_{3-12})$alkyl; hydroxy$(C_{3-12})$alkyl; $(C_{1-12})$alkoxy$(C_{3-12})$alkyl; $(C_{1-12})$alkanoyloxy$(C_{3-12})$alkyl; $(C_{3-6})$cycloalkyl$(C_{3-12})$alkyl; hydroxy-, $(C_{1-12})$alkoxy- or $(C_{1-12})$alkanoyloxy-$(C_{3-6})$cycloalkyl$(C_{3-12})$alkyl; cyano$(C_{3-12})$alkyl; $(C_{2-12})$alkenyl; $(C_{2-12})$alkynyl; tetrahydrofuryl; mono- or di-$(C_{1-12})$alkylamino$(C_{3-12})$alkyl; acylamino$(C_{3-12})$alkyl; $(C_{1-12})$alkyl- or acylaminocarbonyl$(C_{3-12})$alkyl; mono- or di-$(C_{1-12})$alkylamino(hydroxy)$(C_{3-12})$alkyl; optionally substituted phenyl$(C_{1-2})$alkyl, phenoxy$(C_{1-12})$alkyl or phenyl(hydroxy)$(C_{1-2})$alkyl; optionally substituted diphenyl$(C_{1-2})$alkyl; optionally substituted phenyl$(C_{2-3})$alkenyl; optionally substituted benzoyl or benzoylmethyl; optionally substituted heteroaryl$(C_{1-2})$alkyl; and optionally substituted heteroaroyl or heteroaroylmethyl;

or $R^3$ is in the 3-position and $R^2$ and $R^3$ together are a divalent residue $=CR^{5'}R^{6'}$ where $R^{5'}$ and $R^{6'}$ are independently selected from H, $(C_{1-6})$alkyl, $(C_{2-6})$alkenyl, aryl$(C_{1-6})$alkyl and aryl$(C_{2-6})$alkenyl, any alkyl or alkenyl moiety being optionally substituted by 1 to 3 groups selected from those listed above for substituents on $R^3$;

$R^4$ forms a group with $R^3$ as above defined or is a group $—CH_2—R^5$ in which $R^5$ is as defined above:

n is 0, 1 or 2; and

A is NHC(O)NH or NHC(O)O.

In one aspect the invention provides compounds of formula (I) where R1 and R1a are selected from the groups listed above other than trifluoromethyl.

The invention also provides a method of treatment of bacterial infections in mammals, particularly in man, which method comprises the administration to a mammal in need of such treatment of an effective amount of a compound of formula (I) or a pharmaceutically acceptable derivative thereof.

The invention also provides the use of a compound of formula (I) or a pharmaceutically acceptable derivative thereof in the manufacture of a medicament for use in the treatment of bacterial infections in mammals.

The invention also provides a pharmaceutical composition for use in the treatment of bacterial infections in mammals comprising a compound of formula (I), or a pharmaceutically acceptable derivative thereof, and a pharmaceutically acceptable carrier.

Preferably $Z^1$–$Z^5$ are each CH or $Z^1$ is N and $Z^2$–$Z^5$ are each CH.

When $R^1$ or $R^{1a}$ is substituted alkoxy it is preferably $(C_{1-6})$alkoxy substituted by optionally N-substituted amino, piperidyl, guanidino or amidino, more preferably by amino or guanidino. Suitable examples of $R^1$ alkoxy include methoxy, n-propyloxy, i-butyloxy, aminoethyloxy, aminopropyloxy, aminopentyloxy, guanidinopropyloxy, piperidin-4-ylmethyloxy, phthalimido pentyloxy or 2-aminocarbonylprop-2-oxy. Preferably $R^1$ is methoxy, amino$(C_{3-5})$alkyloxy, guanidino$(C_{3-5})$alkyloxy, nitro or fluoro, most preferably methoxy.

Preferably $R^{1a}$ is hydrogen.

Preferably n is 0.

Preferably A is NHCONH.

$R^3$ is preferably hydrogen, $(C_{1-6})$alkyl, $(C_{1-6})$alkenyl, optionally substituted 1-hydroxy-$(C_{1-6})$alkyl, more preferably hydroxymethyl or 1,2-dihydroxy($C_{2-6}$)alkyl wherein the 2-hydroxy group is optionally substituted. Preferred examples of $R^3$ include hydroxymethyl, 1-hydroxyethyl or 1,2-dihydroxyethyl wherein the 2-hydroxy group is optionally substituted with alkylcarbonyl or aminocarbonyl where the amino group is optionally substituted. Other suitable examples of $R^3$ include 2-hydroxyethyl, 2- or 3-hydroxypropyl, ethyl or vinyl.

R3 is preferably in the 3-position.

When $R^2$ and $R^3$ together form a group, this is preferably =CHCH$_3$.

When R3 and R4 together form a group, this is preferably —(CH$_2$)$_4$— optionally substituted by $R^5$. Preferably $R^5$ on this cyclic group is ($C_{4-9}$)alkyl, unsubstituted phenyl($C_{1-2}$)alkyl or unsubstituted phenyl($C_{2-3}$)alkenyl, more preferably n-pentyl or n-hexyl. most preferably n-pentyl.

Suitable groups $R^4$ include n-pentyl, n-hexyl, n-heptyl, n-octyl, n-nonyl, n-decyl, n-dodecyl, methoxybutyl, phenylethyl, phenylpropyl or 3-phenyl-prop-2-en-yl optionally substituted on the phenyl ring, 3-benzoylpropyl, 4-benzoylbutyl, 3-pyridylmethyl, 3-(4-fluorobenzoyl) propyl, cyclohexylmethyl, cyclobutylmethyl, t-butoxycarbonylaminomethyl and phenoxyethyl.

Preferably $R^4$ is ($C_{5-10}$)alkyl, unsubstituted phenyl($C_{2-3}$) alkyl or unsubstituted phenyl($C_{3-4}$)alkenyl, more preferably hexyl, heptyl, 5-methylhexyl, 6-methyl heptyl, 3-phenyl-prop-2-en-yl or 3-phenylpropyl, most preferably n-heptyl.

Most preferably $R^5$ is unbranched at the α and, where appropriate, β positions.

Halo or halogen includes fluoro, chloro, bromo and iodo.

The term 'heterocyclic' as used herein includes aromatic and non-aromatic, single and fused, rings suitably containing up to four hetero-atoms in each ring selected from oxygen, nitrogen and sulphur, which rings may be unsubstituted or substituted by, for example, up to three groups selected from optionally substituted amino. halogen, ($C_{1-6}$) alkyl, ($C_{1-6}$)alkoxy, halo($C_{1-6}$)alkyl, hydroxy, carboxy, carboxy salts, carboxy esters such as ($C_{1-6}$)alkoxycarbonyl, ($C_{1-6}$)alkoxycarbonyl($C_{1-6}$)alkyl, aryl, and oxo groups. Each heterocyclic ring suitably has from 4 to 7, preferably 5 or 6, ring atoms. A fused heterocyclic ring system may include carbocyclic rings and need include only one heterocyclic ring. Compounds within the invention containing a heterocyclyl group may occur in two or more tautometric forms depending on the nature of the heterocyclyl group; all such tautomeric forms are included within the scope of the invention.

Where an amino group forms part of a single or fused non-aromatic heterocyclic ring as defined above suitable optional substituents in such substituted amino groups include ($C_{1-16}$)alkyl optionally substituted by hydroxy, ($C_{1-6}$)alkoxy, thiol, ($C_{1-6}$)alkylthio, halo or trifluoromethyl, and amino-protecting groups such as acyl or ($C_{1-6}$) alkylsulphonyl groups.

The term 'heteroaryl' includes the aromatic heterocyclic groups referred to above. Examples of heteroaryl groups include pyridyl, triazolyl, tetrazolyl, indolyl, thienyl, isoimidazolyl, thiazolyl, furanyl, quinolinyl, imidazolidinyl and benzothienyl.

When used herein the term 'aryl', includes phenyl and naphthyl, each optionally substituted with up to five, preferably up to three, groups selected from halogen, mercapto, ($C_{1-16}$)alkyl, phenyl, ($C_{1-16}$)alkoxy, hydroxy($C_{1-16}$)alkyl, mercapto ($C_{1-6}$)alkyl, halo($C_{1-6}$)alkyl, hydroxy, optionally substituted amino, nitro, carboxy, ($C_{1-6}$)alkylcarbonyloxy, ($C_{1-16}$)alkoxycarbonyl, formyl, or ($C_{1-6}$)alkylcarbonyl groups.

The term 'acyl' includes ($C_{1-16}$)alkoxycarbonyl, formyl or ($C_{1-6}$)alkylcarbonyl group.

Compounds of formula (I) wherein:
$R^3$ is hydroxy($C_{1-6}$)alkyl or 1,2-dihydroxy($C_{2-6}$)alkyl optionally substituted on the hydroxy group(s) as claimed, hereinafter 'compounds of formula (IA)', are particularly preferred.

The invention also provides a pharmaceutical composition comprising a compound of formula (I), or a pharmaceutically acceptable derivative thereof, and a pharmaceutically acceptable carrier.

Some of the compounds of this invention may be crystallised or recrystallised from solvents such as organic solvents. In such cases solvates may be formed. This invention includes within its scope stoichiometric solvates including hydrates as well as compounds containing variable amounts of water that may be produced by processes such as lyophilisation.

Since the compounds of formula (I) are intended for use in pharmaceutical compositions it will readily be understood that they are each provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 59% of a compound of the formula (I) or salt thereof.

Pharmaceutically acceptable derivatives of the above-mentioned compounds of formula (I) include the free base form or their acid addition or quaternary ammonium salts, for example their salts with mineral acids e.g. hydrochloric, hydrobromic or sulphuric acids, or organic acids, e.g. acetic, fumaric or tartaric acids. Compounds of formula (I) may also be prepared as the N-oxide.

Certain of the above-mentioned compounds of formula (I) may exist in the form of optical isomers, e.g. diastereoisomers and mixtures of isomers in all ratios, e.g. racemic mixtures. The invention includes all such forms, in particular the pure isomeric forms.

In a further aspect of the invention there is provided a process for preparing compounds of formula (I), or a pharmaceutically acceptable derivative thereof, which process comprises reacting a compound of formula (IV) with a compound of formula (V):

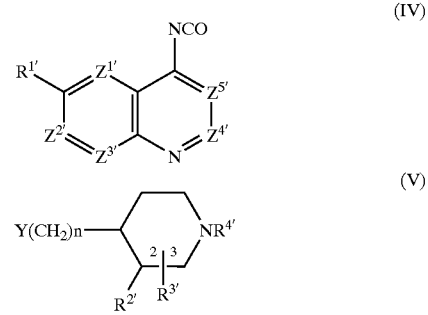

wherein $Z^1$, $Z^2$, $Z^3$, $Z^4$ and $Z^5$, m, n, $R^1$, $R^2$, $R^3$ and $R^4$ are as defined in formula (I), and Y is OH or NH$_2$ in which $Z^{1'}$–$Z^{5'}$ are $Z^1$–$Z^5$ or groups convertible thereto, $R^{1'}$, $R^{2'}$, $R^{3'}$ and $R^{4'}$ are $R^1$, $R^2$, $R^3$ and $R^4$ or groups convertible thereto, and thereafter optionally or as necessary converting $Z^{1'}$–$Z^{5'}$ to $Z^1$–$Z^5$, converting $R^{1'}$, $R^{2'}$, $R^{3'}$ and $R^{4'}$ to $R^1$, $R^2$, $R^3$ and $R^4$, interconverting $R^1$, $R^2$, $R^3$ and/or $R^4$ and forming a pharmaceutically acceptable derivative thereof.

The reaction of the compounds of formulae (IV) and (V) is a standard urea or carbamate formation reaction conducted by methods well known to those skilled in the art (for example see March, J; Advanced Organic Chemistry, Edition 3 (John Wiley and Sons, 1985)). The process is preferably carried out in a polar, non-nucleophilic solvent such as N,N-dimethylformamide.

$R^{1'}$, $R^{2'}$, $R^{3'}$ and $R^{4'}$ are preferably $R^1$, $R^2$, $R^3$ and $R^4$. $R^{1'}$ is preferably methoxy. $R^{2'}$ is preferably hydrogen. $R^{3'}$ is preferably $R^3$ such as hydrogen, vinyl or a carboxy ester-containing group. $R^{4'}$ is preferably H or a protecting group.

Conversions of $R^{1'}$, $R^{2'}$, $R^{3'}$ and $R^{4'}$ and interconversions of $R^1$, $R^2$, $R^3$ and $R^4$ are conventional. In compounds which contain an optionally substituted hydroxy group, suitable conventional hydroxy protecting groups which may be removed without disrupting the remainder of the molecule include acyl and alkylsilyl groups.

For example $R^{1'}$ methoxy is convertible to $R^{1'}$ hydroxy by treatment with lithium and diphenylphosphine (general method described in Ireland et. al. (1973) J.Amer.Chem.Soc.,7829) or HBr. Alkylation of the hydroxy group with a suitable alkyl derivative bearing a leaving group such as halide and a protected amino, piperidyl, amidino or guanidino group or group convertible thereto, yields, after conversion/deprotection, $R^1$ ($C_{1-6}$)alkoxy substituted by optionally N-substituted amino, piperidyl, guanidino or amidino.

Examples of $Z^{1'}$–$Z^{5'}$ are $CR^{1a'}$ where $R^{1a'}$ is a group convertible to $R^{1a}$.

$R^{3'}$ alkenyl is convertible to hydroxyalkyl by hydroboration using a suitable reagent such as 9-borabicyclo[3.3.1] nonane, epoxidation and reduction or oxymercuration.

$R^{3'}$ carboxylate groups may be converted to $R^3$ hydroxymethyl by reduction with a suitable reducing agent such as lithium aluminium hydride.

$R^3$ 1,2-dihydroxy can be prepared from $R^{3'}$ alkenyl using osmium tetroxide or other reagents well known to those skilled in the art (see Advanced Organic Chemistry (Ed. March, J.) (John Wiley and Sons. 1985), p 732–737 and refs. cited therein) or epoxidation followed by hydrolysis (see Advanced Organic Chemistry (Ed. March, J.) (John Wiley and Sons, 1985), p 332,333 and refs. cited therein).

$R^3$ vinyl can be chain extended by standard homologation e.g by conversion to hydroxyethyl followed by oxidation to the aldehyde which is then subjected to a Wittig reaction.

Compounds of formula (I) where $R^2$ and $R^3$ are a divalent residue $=CR^{5'}R^{6'}$ can be prepared by treatment of a compound of formula (I) where $R^3$ is alken-1-yl with a strong base in an aprotic solvent. Suitable bases include $Ph_2PLi$/PhLi (as described in Ireland et. al., J. Amer. Chem. Soc. (1973), 7829), t-BuLi, and suitable solvents include THF and ether.

Substituents on $R^3$ alkyl or alkenyl may be interconverted by conventional methods, for example hydroxy may be derivatised by esterification, acylation or etherification. Hydroxy groups may be converted to halogen, thiol, alkylthio, azido, alkylcarbonyl, amino, aminocarbonyl, oxo, alkylsulphonyl, alkenylsulphonyl or aminosulphonyl by conversion to a leaving group and substitution by the required group or oxidation as appropriate or reaction with an activated acid, isocyanate or alkoxyisocyanate. Primary and secondary hydroxy groups can be oxidised to an aldehyde or ketone respectively and alkyated with a suitable agent such as an organometallic reagent to give a secondary or tertiary alcohol as appropriate.

NH is converted to $NR^4$ by conventional means such as alkylation with an alkyl halide in the presence of base, acylation/reduction or reductive alkylation with an aldehyde.

It will be appreciated that under certain circumstances interconvertions may interfere, for example, the piperidine NH will require protection as an acyl derivative $R^{4'}$, during coupling of the compounds of formulae (IV) and (V) and during conversion of $R^{1'}$, $R^{2'}$ or $R^{3'}$.

Compounds of formulae (IV) and (V) are known compounds) or prepared analogously.

The isocyanate of formula (IV) may be prepared conventionally. A 4-amino derivative such as 4-amino-quinoline, and phosgene, or phosgene equivalent (eg triphosgene) provide the isocyanate or it may be prepared more conveniently from a 4-carboxylic acid by a 'one-pot' Curtius Reaction with diphenyl phosphoryl azide (DPPA) [see T. Shiori et al. Chem. Pharm. Bull. 35, 2698–2704 (1987)].

The 4-carboxy derivatives are commercially available or may be prepared by conventional procedures for preparation of carboxy heteroaromatics well known to those skilled in the art. For example, quinazolines may be prepared by standard routes as described by T. A. Williamson in Heterocyclic Compounds, 6, 324 (1957) Ed. R. C. Elderfield. Pyridazines may be prepared by routes analogous to those described in Comprehensive Heterocyclic Chemistry, Volume 3, Ed A. J. Boulton and A. McKillop and napthyridines may be prepared by routes analogous to those described in Comprehensive Heterocyclic Chemistry, Volume 2, Ed A. J. Boulton and A. McKillop.

The 4-amino derivatives are commercially available or may be prepared by conventional procedures from a corresponding 4-chloro derivative by treatment with ammonia (O. G. Backeberg et. al., J. Chem Soc., 381, 1942.) or propylamine hydrochloride (R. Radinov et. al., Synthesis, 886, 1986).

A 4-chloroquinoline is prepared from the corresponding quinolin-4-one by reaction with phosphorus oxychloride ($POCl_3$) or phosphorus pentachloride, $PCl_5$.

A 4-chloroquinazoline is prepared from the corresponding quinazolin-4-one by reaction with phosphorus oxychloride ($POCl_3$) or phosphorus pentachloride, $PCl_5$. A quinazolinone and quinazolines may be prepared by standard routes as described by T. A. Williamson in Heterocyclic Compounds, 6, 324 (1957) Ed. R. C. Elderfield. Pyridazines may be prepared by routes analogous to those described in Comprehensive Heterocyclic Chemistry, Volume 3, Ed A. J. Boulton and A. McKillop and napthyridines may be prepared by routes analogous to those described in Comprehensive Heterocyclic Chemistry, Volume 2, Ed A. J. Boulton and A. McKillop.

4-Hydroxy-1,5-naphthyridines can be prepared from 3-aminopyridine derivatives by reaction with diethyl ethoxymethylene malonate to produce the 4-hydroxy-3-carboxylic acid ester derivative with subsequent hydrolysis to the acid, followed by thermal decarboxylation in quinoline (as for example described for 4-Hydroxy-[1,5] naphthyridine-3-carboxylic acid, Joe T. Adams et al., J.Amer.Chem.Soc., 1946, 68, 1317). A 4-hydroxy-[1,5] naphthyridine can be converted to the 4-chloro derivative by heating in phosphorus oxychloride. A 4-amino 1,5-naphthyridine can be obtained from the 4-chloro derivative by reaction with n-propylamine in pyridine.

Similarly, 6-methoxy-1,5-naphthyridine derivatives can be prepared from 3-amino-6-methoxypyridine.

1,5-Naphthyridines may be prepared by other methods well known to those skilled in the art (for examples see P. A. Lowe in "Comprehensive Heterocyclic Chemistry" Volume 2, p581–627, Ed A. R. Katritzky and C. W. Rees, Pergamon Press, Oxford, 1984).

The 4-hydroxy and 4-amino-cinnolines may be prepared following methods well known to those skilled in the art [see A. R. Osborn and K. Schofield, *J. Chem. Soc.* 2100 (1955)]. For example, a 2-aminoacetopheneone is diazotised with sodium nitrite and acid to produce the 4-hydroxycinnoline with conversion to chloro and amino derivatives as described for 1,5-naphthyridines.

For compounds of formula (V) where Y is $NH_2$ suitable amines may be prepared from the corresponding acid or alcohol (Y is $CO_2H$ or $CH_2OH$). In a first instance, an N-protected piperidine containing an acid bearing substituent, can undergo a Curtius rearrangement and the intermediate isocyanate can be converted to the amine by standard methods well known to those skilled in the art. For example, an acid-substituted N-protected piperidine can undergo a Curtius rearrangement e.g. on treatment with diphenylphosphoryl azide and beating, and the intermediate isocyanate reacts in the presence of 2-trimethylsilylethanol to give the trimethylsilylethylcarbamate (T. L. Capson & C. D. Poulter, *Tetrahedron Letters*, 1984, 25, 3515). This undergoes cleavage on treatment with tetrabutylammonium fluoride to give the 4-amine-substituted N-protected piperidine.

In a second instance, an N-protected piperidine containing an alcohol bearing substituent undergoes a Mitsunobu reaction (for example as reviewed in Mitsunobu, Synthesis, (1981), 1), for example with succinimide in the presence of diethyl azodicarboxylate and triphenylphosphine to give the phthalimidoethylpiperidine. Removal of the phthaloyl group, for example by treatment with methylhydrazine, gives the amine of formula (V).

Compounds of formula (V) where n=1 or 2 may be prepared from the compound where n=0 by homologation eg starting from a compound of formula (V) where $Y=CO_2H$.

Where $R_3$ and $R_4$ form a group such as $-(CH_2)_4-$, the azabicylic intermediate of formula (V) may be prepared from the ketone such as 1-aza-8-(equatorial)-formyloxy-bicyclo[4,4,0]decan-2-one. This ketone may be prepared by a literature procedure [H. E. Schoemaker et al. *Tetrahedron*, 34, 163–172 (1978)] and hydrolysed to the 8-alcohol with sodium hydroxide. The alcohol may then subjected to a Mitsunobu reaction (diethylazodicarboxylate/triphenyl phosphine) [eg. see K. Y. Ko et al. *J. Org. Chem.* 51, 5353 (1986)]) in the presence of benzoic acid to afford the 8-axial benzoate, which can be hydrolysed with sodium hydroxide in aqueous dioxan to the axial 8-hydroxy-derivative. The hydroxyl may be protected with a trimethylsilyl group and then reacted with LDA (lithium diisopropylamide) and an alkylating agent such as a haloalkane derivative e.g. 1-bromopropane, to give the 3-alkyl derivative (mixture of axial/equatorial isomers at C-3). Reduction of the lactam moiety with lithium aluminium hydride gives the required 8-(ax)-hydroxy-bicyclodecane. Homologous compounds where n=1 or 2 may be prepared by conventional homologation routes, for example by Wittig reaction of the above bicyclic ketone followed by reduction of the alkylene product.

Conversions of $R^{1'}$, $R^{2'}$, $R^{3'}$ and $R^{4'}$ may be carried out on the intermediates of formulae (IV) and (V) prior to their reaction to produce compounds of formula (1) in the same way as described above for conversions after their reaction.

Where a trans-substituted compound of formula (I) is required, a trans-substituted piperidine moiety of formula (V) may be prepared from the corresponding cis isomer of formula (V) having an $R^{3'}$ vinyl group in the 3-position with a substituent that can subsequently be converted to the required group $(CH_2)_nY$ by heating in formaldehyde.

The pharmaceutical compositions of the invention include those in a form adapted for oral, topical or parenteral use and may be used for the treatment of bacterial infection in mammals including humans.

The antibiotic compounds according to the invention may be formulated for administration in any convenient way for use in human or veterinary medicine, by analogy with other antibiotics.

The composition may be formulated for administration by any route, such as oral, topical or parenteral. The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatin, sorbitol, tragacanth, or polyvinylpyrollidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing.

Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, preferably from 10–60% by weight, of the active material, depending on the method of administration. Where the compositions comprise dosage units, each unit will preferably contain from 50–500 mg of the active ingredient. The dosage as employed for adult human treatment will preferably range from 100 to 3000 mg per day, for instance 1500 mg per day depending on the route and frequency of administration. Such a dosage corresponds to 1.5 to 50 mg/kg per day. Suitably the dosage is from 5 to 20 mg/kg per day.

No toxicological effects are indicated when a compound of formula (I) or a pharmaceutically acceptable salt or in vivo hydrolysable ester thereof is administered in the above-mentioned dosage range.

The compound of formula (I) may be the sole therapeutic agent in the compositions of the invention or a combination with a β-lactamase inhibitor may be employed.

Compounds of formula (I) are active against a wide range of organisms including both Gram-negative and Gram-positive organisms.

The following examples illustrate the preparation of certain compounds of formula (I) and the activity of certain compounds of formula (I) against various bacterial organisms.

EXAMPLE 1

1-Aza-8-(ax)-[(6-methoxyquinolin-4-yl)-aminocarbonyloxy]-3-(ax)-n-pentyl-bicyclo[4,4,0] decane (a) 1-Aza-3-n-pentyl-8-(ax)-hydroxy-bicyclo[4,4,0]decan-2-one A 1.5 M solution of lithium dilsopropylamide in cyclohexane (2.25 ml) was added to a solution of 1-aza-8-(ax)-(trimethylsilyloxy)-bicyclo[4,4,0]decan-2-one (0.73 g) (King et al., Bioorg Med Chem Letts., vol.2, p.1147 (1992)) in dry tetrahydrofuran (10 ml) at −78° C. and the solution was stirred for 10 minutes. 1-Bromopropane (0.503 g) was added and the solution was stirred at −78° C. for 1 hour and allowed to warm up to room temperature overnight. The mixture was basified with aqueous sodium bicarbonate solution and evaporated to dryness. It was re-suspended in 1:1 tetrahydrofuran-water (100 ml), acidified to pH 2 with 2 M hydrochloric acid, and stirred at room temperature for 30 minutes. The mixture was basified with 10% sodium carbonate solution, evaporated to dryness, treated with chloroform, dried over sodium sulfate and evaporated to afford an oil.

MS (+ve ion electrospray) m/z 240 (MH+)

(b) 1-Aza-3-n-pentyl-8-(ax)-hydroxy-bicyclo[4,4,0]decane

A solution of 1-aza-3-n-pentyl-8-(ax)-hydroxy-bicyclo[4,4,0]decan-2-one (0.3 g) in dry tetrahydrofuran (5 ml) was treated with lithium aluminium hydride (0.10 g) and the mixture was heated under reflux for 3 hours. The cooled solution was treated dropwise with a solution of 2M sodium hydroxide until a white precipitate had formed. Dichloromethane and anhydrous sodium sulfate were added and the solution was filtered and evaporated to dryness to give an oil (0.26 g).

MS (+ve ion electrospray) m/z 226 (MH+)

(c) Title Compound

A suspension of 6-methoxyquinoline-4-carboxylic acid (0.142 g) in dichloroethane (3 ml) was treated with triethylamine (71 mg) followed by diphenylphosphoryl azide (0.193 g) and the mixture was stirred at room temperature for 1.5 hours. The resultant solution was heated (oil bath temperature 100° C.) for 0.5 hours to form the isocyanate. A solution of 1-aza-3-n-pentyl-8-(ax)-hydroxy-bicyclo[4,4,0] decane (0.125 g) in dichloroethane (1 ml) was added and the solution was heated under reflux for 4 hours. A further batch of isocyanate [(prepared from 6-methoxyquinoline-4-carboxylic acid (47 mg)] in dichloroethane was added and the solution heated under reflux for a further 1 hour, left at room temperature overnight, and evaporated to dryness. The product was dissolved in tetrahydrofuran and basified with aqueous sodium hydroxide, evaporated to dryness, and partitioned between water and chloroform. The organic fraction was dried over sodium sulfate, evaporated and chromatographed on silica gel in ethyl acetate-hexane (1:2) to afford the title compound as a white solid (40 mg), after trituration with ether-hexane.

MS (+ve ion electrospray) m/z 426 (MH+).

EXAMPLE 2

1-Aza-8-(ax)-[(6-methoxyquinolin-4-yl) aminocarbonyloxy]-3-(eq)-n-pentyl-bicyclo[4,4,0] decane Reaction of 6-methoxyquinoline-4-isocyanate prepared from 6-methoxyquinoline4-carboxylic acid (0.142 g) with 1-aza-3-n-pentyl-8-(ax)-hydroxy-bicyclo[4,4,0]decane (0.10 g) (by the Method of Example 1(c)) and chromatography of the product on silica gel in ethyl acetate-hexane (1:1) gave the compound of Example 1 (30 mg). Continued elution with ethyl acetate, followed by preparative TLC [methanol-ethyl acetate (1:10)] gave the title compound as a pale yellow foam (14 mg).

MS (+ve ion electrospray) m/z 426 (MH+).

EXAMPLE 3

1-Heptyl-4-[N-(6-methoxyquinolin-4-yl) aminocarbonyloxy]piperidine (a) 1-Heptyl-4-hydroxypiperidine 4-Hydroxypiperidine was dissolved in N,N-dimethylformamide (20 ml) and treated with potassium carbonate (1.5 g, 10.8 mmol) and 1-iodoheptane (1.8 ml, 11.3 mmol). After stirring for 2 h the mixture was diluted with ethyl acetate, washed with water, brine, dried and evaporated.

(b) Title Compound

6-Methoxyquinoline-4-isocyanate was prepared from the corresponding carboxylic acid (1 g, 4.9 mmol) by the method of Example 1(c). 1-Heptyl-4-hydoxypiperidine (1.0 g, 5.0 mmol) was added and the mixture stirred for 2.5 h. After washing with sodium carbonate and brine the solution was dried and evaporated and the product purified on silica gel eluting with methanol-ethyl acetate (5:95), MH$^+$ 400.

EXAMPLE 4

1-Heptyl-4-(6-methoxyquinolin4-yl)ureidopiperidine (a) 1-Benzyl-4-(6-methoxyquinolin-4-yl)ureidopiperidine 6-Methoxyquinoline-4-isocyanate was prepared from the corresponding carboxylic acid (1 g, 4.9 mmd) by the method of Example 1(c) and 4-amino-1-benzyl piperidine (1.0 ml, 5.0 mmol) was added. After stirring for 3 h the mixture was diluted with dichloromethane, washed with sodium carbonate solution, brine, dried and evaporated. Purification on silica gel eluting with methanol-ethyl acetate mixtures gave a yellow solid (0.51 g, 27%) MH$^+$ 391.

(b) Title Compound

The product from Example 4(a) (0.50 g, 1.28 mmol) in methanol (25 ml) was hydrogenated over 10% palladium on charcoal (0.30 g) for 4 days. The mixture was filtered through celite and evaporated. The residue was dissolved in N,N-dimethylformamide (10 ml) and treated with 1-iodoheptane (0.24 ml, 1.5 mmol) and potassium carbonate (0.21 g, 1.5 mmol). After stirring for 18 h the mixture was diluted with ethyl acetate, washed with water, brine, dried and evaporated. Purification on silica gel eluting with methanol-chloroform-ammonia (5:95:0.5) gave a yellow solid (0.27 g, 55%), $MH^+$ 399.

EXAMPLE 5

N-(cis-1-Heptyl-3-(R/S)-hydroxymethyl-4-(S/R)-piperidyl)-N'-(6-methoxyquinolin-4-yl)urea oxalate (a) 4-Benzylamino-1-tert-butoxycarbonyl-3-ethoxycarbonyl-1,2,5,6-tetrahydropyridine A solution of 1-tert-butoxycarbonyl-3-ethoxycarbonylpiperidin-4-one (prepared from 3-ethoxycarbonylpiperidin-4-one and di-tert-butyl-dicarbonate in dichloromethane and triethylamine) (25 g) and benzylamine (10.85 g) in toluene was heated under reflux in a Dean and Stark apparatus for 18 hours and then evaporated to dryness to give an oil.

(b) cis-4-(S/R)-Benzylamino-1-tert-butoxycarbonyl-3-(R/S)-ethoxycarbonylpiperidine The enamine (5a) (25 g) in ethanol (300 ml) was hydrogenated over platinum oxide (1.5 g) for 4 days, filtered, and evaporated to dryness. It was chromatographed on silica gel (ethyl acetate-hexane) to afford the title compound as an oil.

MS (+ve ion electrospray) m/z 363 (MH+).

(c) cis-4-(S/R)-Amino-1-tert-butoxycarbonyl-3-(R/S)-ethoxycarbonylpiperidine

The amine (5b) (4 g) in ethanol (80 ml) containing acetic acid (0.73 g) was hydrogenated at 50 psi (Parr reaction vessel) over 10% palladium-carbon (10 g) for 18 hours, filtered and evaporated to dryness to afford the acetate salt of the title compound as a white solid (3 g).

MS (+ve ion electrospray) m/z 273 (MH+).

It was converted to the oily free base by extraction using dichloromethane-sodium carbonate and drying over sodium sulfate.

(d) N-(cis-1-tert-Butoxycarbonyl-3-(R/S)-ethoxycarbonyl-4-(S/R)-piperidyl)-N'-(6-methoxyquinolin-4-yl)urea A suspension of 6-methoxyquinoline-4-carboxylic acid (0.98 g) in dry toluene (50 ml) was treated with triethylamine (1.95 g) followed by diphenylphosphoryl azide (1.39 g) and the mixture was stirred at room temperature for 8 hours. The resultant solution was treated with the amine (5c) and then heated under reflux for 4 hours and evaporated to dryness. The product was chromatographed on silica gel (ethyl acetate-hexane) to afford the title compound (1.98 g) as a foam.

MS (+ve ion electrospray) m/z 473 (MH+).

(e) N-(cis-3-(R/S)-Ethoxycarbonyl-4-(S/R)-piperidyl)-N'-(6-methoxyquinolin-4-yl)urea The urea (5d) (1.0 g) was treated with dichloromethane (30 ml) and trifluoroacetic acid (20 ml) at room temperature for 3 hours and evaporated to dryness. It was basified with sodium carbonate solution and evaporated to dryness. The solid was extracted three times with ethanol-chloroform (1:9) and evaporated to dryness to afford a foam (0.75 g).

MS (+ve ion electrospray) m/z 373 (MH+).

(f) N-(cis-3-(R/S)-Ethoxycarbonyl-1-heptyl-4-(S/R)-piperidyl)-N'-(6-methoxyquinolin-4-yl)urea oxalate The amine (5e) (0.75 g) in dry ethanol (15 ml) was treated with heptaldehyde (0.636 g) and sodium triacetoxyborohydride (0.459 g) for 1 hour at room temperature. Sodium bicarbonate solution was added and the mixture was extracted with dichloromethane, dried over sodium sulfate, and evaporated to afford an oil. Chromatography on silica gel (ethyl acetate-hexane) gave the title compound (0.68 g) as an oil.

MS (+ve ion electrospray) m/z 471 (MH+).

The free base in dichloromethane was treated with 1 molar equivalent of oxalic acid in ether and the resulting solid was collected, triturated with ether, to afford the oxalate salt as a white solid.

(g) Title Compound

The ester (5f) (0.12 g) in dry tetrahydrofuran (4 ml) at 0° C. was treated with lithium aluminium hydride (0.655 ml of a 1M solution in ether) for 5 hours, and at room temperature for 1 hour, then it was quenched by the addition of 2M sodium hydroxide. Dichloromethane and sodium sulfate were added and the solution was filtered and evaporated to dryness. The product was chromatographed on silica gel (methanol-dichloromethane) to afford the title compound (0.055 g), as the oily free base.

MS (+ve ion electrospray) m/z 429 (MH+).

The free base in dichloromethane was converted to the oxalate salt in the normal manner, affording a white solid.

EXAMPLE 6

N-(cis-1-Heptyl-3-(R/S)-hydroxymethyl-4-(S/R)-piperidyl)-N'-(6-methoxy-[1,5]-naphthyridin-4-yl) urea Oxalate (a) 4-Hydroxy-6-methoxy-[1,5]naphthyridine-3-carboxylic Acid Ethyl Ester 3-Amino-6-methoxypyridine (12.41 g) and diethyl ethoxymethylene malonate (20.2 ml) in Dowtherm A (400 ml) were heated at reflux. under argon for 1 hour. The cooled reaction mixture was poured into pentane (1 litre). The precipitated solid was collected by filtration, washed with pentane and dried to afforded a solid (24.78 g, crude).

(b) 4-Hydroxy-6-methoxy-[1,5]naphthyridine-3-carboxylic Acid

The ester (6a) (0.642 g) in 10% aqueous sodium hydroxide (115 ml) was heated at reflux for 1.5 hours. The reaction mixture was cooled then acidified with glacial acetic acid. The precipitated solid was collected by filtration, washed with water and dried in vacuo to afford a beige solid (0.542 g).

MS (+ve ion electrospray) m/z 221 ($MH^+$).

(c) 4-Chloro-6-methoxy-[1,5]naphthyridine

The acid (6b) (6.82 g) was heated in quinoline (20 ml) at reflux for 2 hours, the mixture was cooled and poured into ether (200 ml) and the orange solid was filtered and washed with ether (5×200 ml). A sample (3.87 g) of the dried solid was treated with phosphorus oxychloride (30 ml) at room temp for 3 hours, the solvent was removed in vacuo and the residue quenched with crushed ice (200 g). The mixture was basified with ammonia solution and filtered. The solid was washed with dichloromethane (10×100 ml), which was evaporated and chromatographed on silica gel (dichloromethane as eluent) to give a yellow solid (3.0 g).

MS (+ve ion electrospray) m/z 195, 197 ($MH^+$).

(d) 4-Amino-6-methoxy-[1,5]naphthyridine

A solution of the chloro compound (6c) (2.0 g) in pyridine (30 ml) was treated with n-propylamine hydrochloride (6.0 g) and the mixture heated at reflux for 16 hours. The reaction mixture was cooled and partitioned between water and ethyl acetate. The aqueous phase was washed with ethyl acetate, the combined organics dried ($Na_2SO_4$) and the solvent removed under reduced pressure. Purification by chromatography on silica gel (5–10% methanol in dichloromethane) afforded a yellow solid (1.0 g).

$^1$H NMR (CDCl$_3$) δ: 4.05 (3H, s), 5.36 (2H, bs), 6.71 (1H, d, J=5 Hz), 7.08 (1H, d, J=9 Hz), 8.10 (1H, d, J=9 Hz), 8.40 (1H, d, J=5 Hz).

MS (+ve ion electrospray) m/z: 176 (MH$^+$).

(e) N-(cis-1-tert-Butoxycarbonyl-3-(R/S)-ethoxycarbonyl-4-(S/R)-piperidyl)-N'-(6-methoxy-[1,5]-naphthyridin-4-yl)urea To a solution of amine (6d) (0.5 g) in chloroform (4 ml) was added 1,1'-carbonyldiimidazole (0.76 g) and dimethylaminopyridine (0.38 g) and the solution was stirred at room temperature for 3.5 hours and evaporated to dryness. The product was heated at 100° C. in dry DMF (7 ml) containing the amine (5c) (0.85 g,), for 3 hours. Aqueous sodium carbonate was added and the mixture was extracted with dichloromethane, dried over sodium sulfate, and evaporated to afford a foam. Chromatography on silica gel (ethyl acetate-hexane) gave an oil (0.928 g).

MS (+ve ion electrospray) m/z 474 (MH+).

(f) N-(cis-3-(R/S)-Ethoxycarbonyl-4-(S/R)-piperidyl)-N'-(6-methoxy-[1,5]-naphthyridine-4-yl)urea The urea (6e) (0.92 g) was treated with dichloromethane (20 ml) and trifluoroacetic acid (30 ml) at room temperature for 3 hours and evaporated to dryness. It was basified with sodium carbonate solution and evaporated to dryness. The solid was extracted three times with warm ethanol-chloroform (1:9) and evaporated to dryness to afford a foam (0.80 g).

MS (+ve ion electrospray) m/z 374 (MH+).

(g) N-(cis-3-(R/S)-Ethoxycarbonyl-1-heptyl-4-(S/R)-piperidyl)-N'-(6-methoxy-[1,5]-naphthyridin-4-yl)urea oxalate The amine (6f) (0.80 g) in dry ethanol (20 ml) was treated with heptaldehyde (0.26 g) and sodium triacetoxyborohydride (0.82 g) for 1 hour at room temperature. Sodium bicarbonate solution was added and the mixture was extracted with dichloromethane, dried over sodium sulfate, and evaporated to afford an oil. Chromatography on silica gel (ethyl acetate-hexane) gave the title compound (0.72 g) as an oil.

MS (+ve ion electrospray) m/z 472 (MH+).

The free base in dichloromethane was treated with 1 molar equivalent of oxalic acid in ether and the resulting solid was collected, triturated with ether, to afford the oxalate salt as a white solid.

(h) Title Compound

The ester (6 g) (0.10 g) in dry tetrahydrofuran (7 ml) was treated with lithium aluminium hydride (0.42 ml of a 1M solution in ether) at 0° C. for 1.5 hours and at room temperature for 2 hours, then it was quenched by the addition of 2M sodium hydroxide. Dichloromethane and sodium sulfate were added and the solution was filtered and evaporated to dryness. The product was chromatographed on silica gel (methanol-dichloromethane) to afford the title compound (0.074 g), as the oily free base.

MS (+ve ion electrospray) m/z 430(MH+). $^1$H NMR (CDCl$_3$) δ: 0.88 (3H, t), 1.20 (9H, bs), 1.40 (2H, bs), 1.9–2.4 (6H, m), 2.50 (1H, bd), 2.90 (2H, m), 3.90 (2H, m), 4.10 (3H, s), 4.17 (1H, m) 6.60 (1H, bd), 7.10 (1H, d), 8.20 (1H, d), 8.38 (1H, d), 8.61 (1H, d), 8.78 (1H, s).

The free base in dichloromethane was converted to the oxalate salt in the normal manner. affording a white solid.

EXAMPLE 7

N-(1-Heptyl-4-piperidyl-N'-(6-methoxy-1,5-naphthyridin-4-yl)urea Oxalate

A solution of the amine (6d) (0.08, 0.5 mmol) in chloroform (2 ml) was treated with N,N-dimethylaminopyridine (0.06 g, 0.5 mmol) then 1,1'-carbonyldiimidazole (0.11 g, 0.7 mmol). After 2 hours the chloroform was removed by evaporation and the residue treated with a solution of 4-amino-1-heptylpiperidine (0.1 g, 0.5 mmol) in N,N-dimethylformamide (1 ml) and the mixture heated to 100° C. for 1 hour. Water (2 ml) was added dropwise and filtration gave a white solid. Chromatography on silica eluting with a methanol in ethyl acetate gradient afforded the title compound as a white solid, (0.1 g, 50%).

$^1$H NMR (CD$_3$OD) 0.80 (3H, t), 1.20 (8H, m), 1.50 (4H, m), 1.90 (2H, m), 2.10 (2H, m), 2.25 (2H, m), 2.85 (2H, m), 3.55(1H,m), 4.00 (3H, s), 7.10 (1H, d), 8.00 (1H, d), 8.20 (1H, d), 8.35 (1H, d).

The following example was prepared by procedures analogous to those described herein:

EXAMPLE 8

1-Aza-8-(ax)-[(6-methoxyquinolin-4yl)-aminocarbonyloxy]-3-(ex)-n-hexyl-bicyclo[4,4,0]decane Biological Activity The MIC (μg/ml) of compounds 1, 3 and 4 against various organisms was determined.

Examples 1, 5, 6 and 7 have an MIC of less than or equal to 1 μg/ml against one or more of a range of gram positive and gram negative bacteria.

The remaining compounds 2, 3, 4 and 8 showed an MIC of less than or equal to 16 μ/ml against one or more of a range of gram positive and gram negative bacteria. (See table 1).

TABLE 1

| Organism | Example 1 | Example 3 | Example 4 | Example 5 | Example 6 | Example 7 |
|---|---|---|---|---|---|---|
| S. aureus Oxford | 2 | 8 | 16 | 1 | 0.5 | 1 |
| S. aureus WCUH29 | 4 | 4 | 8 | 1 | 1 | 1 |
| S. aureus Carter 37 | 8 | 8 | 16 | ND | ND | ND |
| E. faecalis I | 8 | 8 | 8 | 4 | 8 | 8 |
| M. catarrhalis Ravasio | 32 | 16 | ND | ND | ND | ND |
| S. pneumoniae R6 | 1 | 4 | 2 | ND | ND | ND |

What is claimed is:

1. A compound of formula (I):

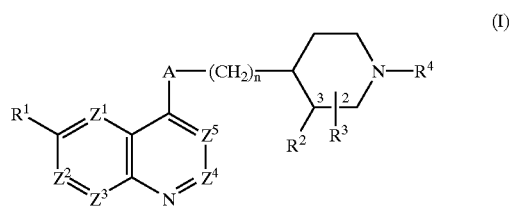

wherein:
one of $Z^1$, $Z^2$, $Z^3$, $Z^4$ and $Z^5$ is $CR^{1a}$ and the remainder are CH, or one of $Z^1$, $Z^2$, and $Z^3$ is N and the remainder are CH;

$R^1$ is selected from hydroxy; $(C_{1-6})$ alkoxy optionally substituted by $(C_{1-6})$alkoxy, amino, piperidyl, guanidino or amidino optionally N-substituted by one or two $(C_{1-6})$alkyl, acyl or $(C_{1-6})$alkylsulphonyl groups, NH$_2$CO, hydroxy, thiol, $(C_{1-6})$alkylthio, heterocyclylthio, heterocyclyloxy, arylthio, aryloxy, acylthio, acyloxy or $(C_{1-6})$alkylsulphonyloxy; $(C_{1-6})$ alkoxy-substituted $(C_{1-6})$alkyl; halogen; $(C_{1-6})$alkyl; $(C_{1-6})$alkylthio; nitro; trifluoromethyl; azido; acyl; acyloxy; acylthio; $(C_{1-6})$alkylsulphonyl; $(C_{1-6})$ alkylsulphoxide; arylsulphonyl; arylsulphoxide or an amino, piperdyl, guanidino or amidino group optionally N-substituted by one or two $(C_{1-6})$alkyl, acyl or $(C_{1-6})$alkylsulphonyl groups, wherein acyl is selected from $(C_{1-6})$alkoxycarbonyl, formyl and $(C_{1-6})$ alkylcarbonyl, or when one of $Z^1$, $Z^2$, and $Z^3$ is N, $R^1$ may instead be hydrogen;

$R^{1a}$ is selected from hydrogen and the groups listed above for $R^1$;

either $R^2$ is hydrogen; and $R^3$ is in the 2- or 3-position and is hydrogen or $(C_{1-6})$alkyl or $(C_{2-6})$alkenyl optionally substituted with 1 to 3 groups selected from:

thiol; halogen; $(C_{1-6})$alkylthio; trifluoromethyl; azido; $(C_{1-6})$alkoxycarbonyl; $(C_{1-6})$alkylcarbonyl; $(C_{2-6})$ alkenyloxycarbonyl; $(C_{2-6})$alkenylcarbonyl; hydroxy optionally substituted by $(C_{1-6})$alkyl, $(C_{2-6})$alkenyl, $(C_{1-6})$alkoxycarbonyl, $(C_{1-6})$ alkylcarbonyl, $(C_{2-6})$alkenyloxycarbonyl, $(C_{2-6})$ alkenylcarbonyl or aminocarbonyl wherein the amino group is optionally substituted by $(C_{1-6})$alkyl, $(C_{2-6})$alkenyl, $(C_{1-6})$alkylcarbonyl or $(C_{2-6})$ alkenylcarbonyl; amino optionally mono- or disubstituted by $(C_{1-6})$alkoxycarbonyl, $(C_{1-6})$ alkylcarbonyl, $(C_{2-6})$alkenyloxycarbonyl, $(C_{2-6})$ alkenylcarbonyl, $(C_{1-6})$alkyl, $(C_{2-6})$alkenyl, $(C_{1-6})$ alkylsulphonyl, $(C_{2-6})$alkenylsulphonyl or aminocarbonyl wherein the amino group is optionally substituted by $(C_{1-6})$alkyl or $(C_{2-6})$alkenyl; aminocarbonyl wherein the amino group is optionally mono- or disubstituted by $(C_{1-6})$alkyl, $(C_{2-6})$alkenyl, $(C_{1-6})$alkoxycarbonyl, $(C_{1-6})$alkylcarbonyl, $(C_{2-6})$ alkenyloxycarbonyl or $(C_{2-6})$alkenylcarbonyl; oxo; $(C_{1-6})$alkylsulphonyl; $(C_{2-6})$alkenylsulphonyl; or $(C_{1-6})$aminosulphonyl wherein the amino group is optionally substituted by $(C_{1-6})$alkyl or $(C_{2-6})$ alkenyl;

or when $R^3$ is in the 2-position it may with $R^4$ form a $C_{3-5}$ alkylene group optionally substituted by a group $R^5$ selected from:

$(C_{3-12})$alkyl; hydroxy$(C_{3-12})$alkyl; $(C_{1-12})$alkoxy $(C_{3-12})$alkyl; $(C_{1-12})$alkanoyloxy$(C_{3-12})$alkyl; $(C_{3-6})$ cycloalkyl$(C_{3-12})$alkyl; hydroxy-, $(C_{1-12})$alkoxy- or $(C_{1-12})$alkanoyloxy-$(C_{3-6})$cycloalkyl$(C_{3-12})$alkyl; cyano$(C_{3-12})$alkyl; $(C_{2-12})$alkenyl; $(C_{2-12})$alkynyl; tetrahydrofuryl; mono- or di-$(C_{1-12})$alkylamino $(C_{3-12})$alkyl; acylamino$(C_{3-12})$alkyl; $(C_{1-12})$alkyl- or acylaminocarbonyl$(C_{3-12})$alkyl; mono- or di- $(C_{1-12})$ alkylamino(hydroxy)$(C_{3-12})$alkyl; optionally substituted phenyl$(C_{1-2})$alkyl, phenoxy$(C_{1-2})$alkyl or phenyl(hydroxy)$(C_{1-2})$alkyl; optionally substituted diphenyl$(C_{1-2})$alkyl; optionally substituted phenyl $(C_{2-3})$alkenyl; optionally substituted benzoyl or benzoylmethyl; optionally substituted heteroaryl$(C_{1-2})$ alkyl; and optionally substituted heteroaroyl or heteroaroylmethyl, wherein acyl is selected from $(C_{1-6})$alkoxycarbonyl, formyl and $(C_{1-6})$ alkylcarbonyl;

or $R^3$ is in the 3-position and $R^2$ and $R^3$ together are a divalent residue $=CR^{5^1}R^{6^1}$ where $R^{5^1}$ and $R^{6^1}$ are independently selected from H, $(C_{1-6})$alkyl, $(C_{2-6})$ alkenyl, aryl$(C_{1-6})$alkyl and aryl$(C_{2-6})$alkenyl, any alkyl or alkenyl moiety being optionally substituted by 1 to 3 groups selected from those listed above for substituents on $R^3$;

$R^4$ forms a group with $R^3$ as above defined or is a group —$CH_2$—$R^5$ in which $R^5$ is as defined above;

n is 0, 1 or 2; and

A is NHC(O)NH or NHC(O)O;

an N-oxide of a compound of formula (I), or a pharmaceutically acceptable salt of a compound of formula (I) or its N-oxide.

2. A compound according to claim 1 wherein $Z^1$–$Z^5$ are each CH or $Z^1$ is N and $Z^2$–$Z^5$ are each CH.

3. A compound according to claim 1 wherein $R^1$ is methoxy, amino$(C_{3-5})$alkyloxy, guanidino$(C_{3-5})$alkyloxy, nitro or fluoro.

4. A compound according to claim 1 wherein A is NHCONH and n is 0.

5. A compound according to claim 1 wherein $R^3$ is in the 3-position and is hydroxy$(C_{1-6})$alkyl or 1,2-dihydroxy$(C_{2-6})$ alkyl optionally substituted on the hydroxy group(s).

6. A compound according to claim 1 wherein $R^4$ is $(C_{5-10})$alkyl, unsubstituted phenyl$(C_{2-3})$alkyl or unsubstituted phenyl$(C_{3-4})$alkenyl.

7. A compound according to claim 1 selected from:

1-aza-8-(ax)-[(6-methoxyquinolin-4-yl)-aminocarbonyloxy]-3-(ax)-n-pentyl-bicyclo[4,4,0] decane;

1-aza-8-(ax)-[(6-methoxyquinolin-4-yl)-aminocarbonyloxy]-3-(eq)-n-pentyl-bicyclo[4,4,0] decane;

1-heptyl-4-[N-(6-methoxyquinolin-4-yl) aminocarbonyloxy]piperidine;

1-heptyl-4-(6-methoxyquinolin-4-yl)ureidopiperidine;

N-(cis-1-heptyl-3-(R/S)-hydroxymethyl-4-(S/R)-piperidyl)-N'-(6-methoxyquinolin-4-yl)urea;

N-(cis-1-heptyl-3-(R/S)-hydroxymethyl-4-(S/R)-piperidyl)-N'-(6-methoxy-[1,5]-naphthyridin-4-yl) urea;

N-(1-heptyl-4-piperidyl-N'-(6-methoxy-1,5-naphthyridin-4-yl)urea;

1-aza-8-(ax)-[(6-methoxyquinolin-4-yl)-aminocarbonyloxy]-3-(ex)-n-hexyl-bicyclo[4,4,0] decane;

an N-oxide of any of the foregoing compounds, or a pharmaceutically acceptable salt of any of the foregoing compounds or an N-oxide thereof.

8. A process for preparing a compound of formula (I), an N-oxide of a compound of formula (I), or a pharmaceutically acceptable salt of a compound of formula (I) or its N-oxide according to claim 1, which process comprises reacting a compound of formula (IV) with a compound of formula (V):

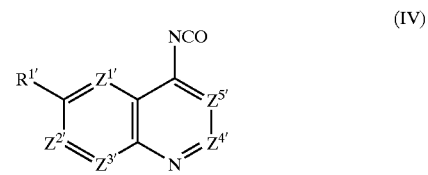

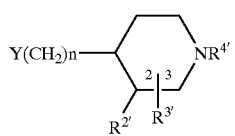

(V)

wherein Y is OH or $NH_2$, $Z^{1'}$–$Z^{5'}$ are, respectively, $Z^1$–$Z^5$ or groups convertible thereto, $R^{1'}$, $R^{2'}$, $R^{3'}$ and $R^{4'}$ are, respectively, $R^1$, $R^2$, $R^3$ and $R^4$ or groups convertible thereto, and $Z^1$, $Z^2$, $Z^3$, $Z^4$, $Z^5$, m, n, $R^1$, $R^2$, $R^3$ and $R^4$ are as defined in formula (I), and thereafter optionally or as necessary converting $Z^{1'}$–$Z^{5'}$ to $Z^1$–$Z^5$, converting $R^{1'}$, $R^{2'}$, $R^{3'}$ and $R^{4'}$ to $R^1$, $R^2$, $R^3$ and $R^4$, interconverting $R^1$, $R^2$, $R^3$ and/or $R^4$ and forming an N-oxide thereof, or a pharmaceutically acceptable salt thereof or its N-oxide.

9. A pharmaceutical composition comprising a compound of formula (I), an N-oxide of a compound of formula (I), or a pharmaceutically acceptable salt of a compound of formula (I) or its N-oxide according to claim 1, and a pharmaceutically acceptable carrier.

10. A method of treatment of bacterial infections in mammals, which method comprises the administration to a mammal in need of such treatment of an effective amount of a compound of formula (I), an N-oxide of a compound of formula (I), or a pharmaceutically acceptable salt of a compound of formula (I) or its N-oxide according to claim 1.

11. A method according to claim 10, wherein said mammal is a human.

12. A compound according to claim 2 wherein $R^1$ is methoxy, amino($C_{3-5}$)alkyloxy, guanidino($C_{3-5}$)alkyloxy, nitro or fluoro.

13. A compound according to claim 2 wherein A is NHCONH and n is 0.

14. A compound according to claim 2 wherein $R^3$ is in the 3-position and is hydroxy($C_{1-16}$)alkyl or 1,2-dihydroxy($C_{2-6}$)alkyl optionally substituted on the hydroxy group(s).

15. A compound according to claim 2 wherein $R^4$ is ($C_{5-10}$)alkyl, unsubstituted phenyl($C_{2-3}$)alkyl or unsubstituted phenyl($C_{3-4}$)alkenyl.

16. A compound according to claim 12 wherein A is NHCONH and n is 0, $R^3$ is in the 3-position and is hydroxy($C_{1-6}$)alkyl or 1,2-dihydroxy($C_{2-6}$)alkyl optionally substituted on the hydroxy group(s), and $R^4$ is ($C_{5-10}$)alkyl, unsubstituted phenyl($C_{2-3}$)alkyl or unsubstituted phenyl($C_{3-4}$)alkenyl.

* * * * *